US009119636B2

(12) United States Patent
Vegesna et al.

(10) Patent No.: US 9,119,636 B2
(45) Date of Patent: Sep. 1, 2015

(54) DISPERSIVE BELT FOR AN ABLATION SYSTEM

(75) Inventors: Venkata Vegesna, Sunnyvale, CA (US); Paul A. Roche, San Jose, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 474 days.

(21) Appl. No.: 13/470,422

(22) Filed: May 14, 2012

(65) Prior Publication Data

US 2012/0330304 A1 Dec. 27, 2012

Related U.S. Application Data

(60) Provisional application No. 61/501,580, filed on Jun. 27, 2011.

(51) Int. Cl.
*A61B 18/14* (2006.01)
*A61B 18/16* (2006.01)
*A61B 17/32* (2006.01)
*A61B 18/18* (2006.01)
*A61B 18/00* (2006.01)

(52) U.S. Cl.
CPC ......... *A61B 18/16* (2013.01); *A61B 17/320068* (2013.01); *A61B 18/1492* (2013.01); *A61B 18/1815* (2013.01); *A61B 2018/00357* (2013.01); *A61B 2018/00577* (2013.01); *A61B 2018/00779* (2013.01); *A61B 2018/00791* (2013.01); *A61B 2018/1467* (2013.01)

(58) Field of Classification Search
USPC .................. 606/32, 35, 34, 41, 36–40, 44–52
See application file for complete search history.

(56) References Cited

U.S. PATENT DOCUMENTS

| 4,763,660 | A | 8/1988 | Kroll et al. |
|---|---|---|---|
| 5,254,088 | A | 10/1993 | Lundquist et al. |
| 5,295,482 | A | 3/1994 | Clare et al. |
| 5,383,874 | A | 1/1995 | Jackson et al. |
| 5,385,146 | A | 1/1995 | Goldreyer |
| 5,391,199 | A | 2/1995 | Ben-Haim |
| 5,398,683 | A | 3/1995 | Edwards et al. |
| 5,500,012 | A | 3/1996 | Brucker et al. |

(Continued)

FOREIGN PATENT DOCUMENTS

| EP | 1343427 81 | 9/2003 |
|---|---|---|
| EP | 1343428 61 | 9/2003 |

OTHER PUBLICATIONS

Goldberg, S. Nahum et al., "Variables Affecting Proper System Grounding for Radiofrequency Ablation in an Animal Model", JVIR, vol. 11, No. 8, Sep. 2000, pp. 1069-1075.

(Continued)

*Primary Examiner* — Paula J Stice
(74) *Attorney, Agent, or Firm* — Faegre Baker Daniels LLP

(57) ABSTRACT

An electrosurgery system includes a catheter including one or more active electrodes adapted to be positioned adjacent biological tissue at an in vivo treatment site in a patient and to deliver electrical energy to the biological tissue. The electrosurgery system further includes a dispersive electrode assembly including a conductive element having a first end and a second end. The dispersive electrode assembly is configured to surround a waist of the patient such that a first surface of the conductive element is in contact with the waist and the first end of the conductive element is adjacent the second end of the conductive element.

15 Claims, 2 Drawing Sheets

(56) References Cited

U.S. PATENT DOCUMENTS

| | | | |
|---|---|---|---|
| 5,520,683 | A | 5/1996 | Subramaniam et al. |
| 5,579,764 | A | 12/1996 | Goldreyer |
| 5,582,609 | A | 12/1996 | Swanson et al. |
| 5,647,870 | A | 7/1997 | Kordis et al. |
| 6,050,994 | A | 4/2000 | Sherman |
| 6,059,778 | A | 5/2000 | Sherman |
| 6,064,905 | A | 5/2000 | Webster, Jr. et al. |
| 6,070,094 | A | 5/2000 | Swanson et al. |
| 6,116,027 | A | 9/2000 | Smith et al. |
| 6,171,305 | B1 | 1/2001 | Sherman |
| 6,200,314 | B1 | 3/2001 | Sherman |
| 6,233,491 | B1 | 5/2001 | Kordis et al. |
| 6,488,678 | B2 | 12/2002 | Sherman |
| 6,579,278 | B1 | 6/2003 | Bencini |
| 6,735,465 | B2 | 5/2004 | Panescu |
| 6,796,980 | B2 | 9/2004 | Hall |
| 6,837,884 | B2 | 1/2005 | Woloszko |
| 6,917,834 | B2 | 7/2005 | Koblish et al. |
| 6,922,579 | B2 | 7/2005 | Taimisto et al. |
| 6,950,689 | B1 | 9/2005 | Willis et al. |
| 7,047,068 | B2 | 5/2006 | Haissaguerre |
| 7,097,643 | B2 | 8/2006 | Cornelius et al. |
| 7,247,155 | B2 | 7/2007 | Hoey et al. |
| 7,347,857 | B2 | 3/2008 | Anderson et al. |
| 7,438,714 | B2 | 10/2008 | Phan |
| 7,569,052 | B2 | 8/2009 | Phan et al. |
| 7,740,629 | B2 | 6/2010 | Anderson et al. |
| 7,799,025 | B2 | 9/2010 | Wellman |
| 7,819,863 | B2 | 10/2010 | Eggers et al. |
| 2002/0087208 | A1 | 7/2002 | Koblish et al. |
| 2004/0215186 | A1 | 10/2004 | Cornelius et al. |
| 2005/0059862 | A1 | 3/2005 | Phan |
| 2005/0059962 | A1 | 3/2005 | Phan et al. |
| 2006/0089634 | A1 | 4/2006 | Anderson et al. |
| 2006/0161146 | A1 | 7/2006 | Cornelius et al. |
| 2006/0247607 | A1 | 11/2006 | Cornelius et al. |
| 2006/0253116 | A1 | 11/2006 | Avitall et al. |
| 2007/0049925 | A1 | 3/2007 | Phan et al. |
| 2007/0055225 | A1* | 3/2007 | Dodd et al. ............... 606/34 |
| 2007/0270794 | A1 | 11/2007 | Anderson et al. |
| 2008/0058836 | A1 | 3/2008 | Moll et al. |
| 2008/0140065 | A1 | 6/2008 | Rioux et al. |
| 2008/0195089 | A1 | 8/2008 | Thiagalingam et al. |
| 2008/0281322 | A1 | 11/2008 | Sherman et al. |
| 2009/0048591 | A1 | 2/2009 | Ibrahim et al. |
| 2009/0093811 | A1 | 4/2009 | Koblish et al. |
| 2009/0099472 | A1* | 4/2009 | Remmert et al. .......... 600/534 |
| 2009/0171341 | A1* | 7/2009 | Pope et al. ............... 606/34 |
| 2009/0240247 | A1 | 9/2009 | Rioux et al. |
| 2010/0010487 | A1 | 1/2010 | Phan et al. |
| 2010/0106155 | A1 | 4/2010 | Anderson et al. |
| 2010/0331658 | A1 | 12/2010 | Kim et al. |

OTHER PUBLICATIONS

Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.

Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.

Patriciu, A. et al., "Detecting Skin Burns Induced by Surface Electrodes", published in Engineering in Medicine and Biology Society, 2001, Proceedings of the 23rd Annual International Conference of the IEEE, vol. 3, pp. 3129-3131.

Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.

\* cited by examiner

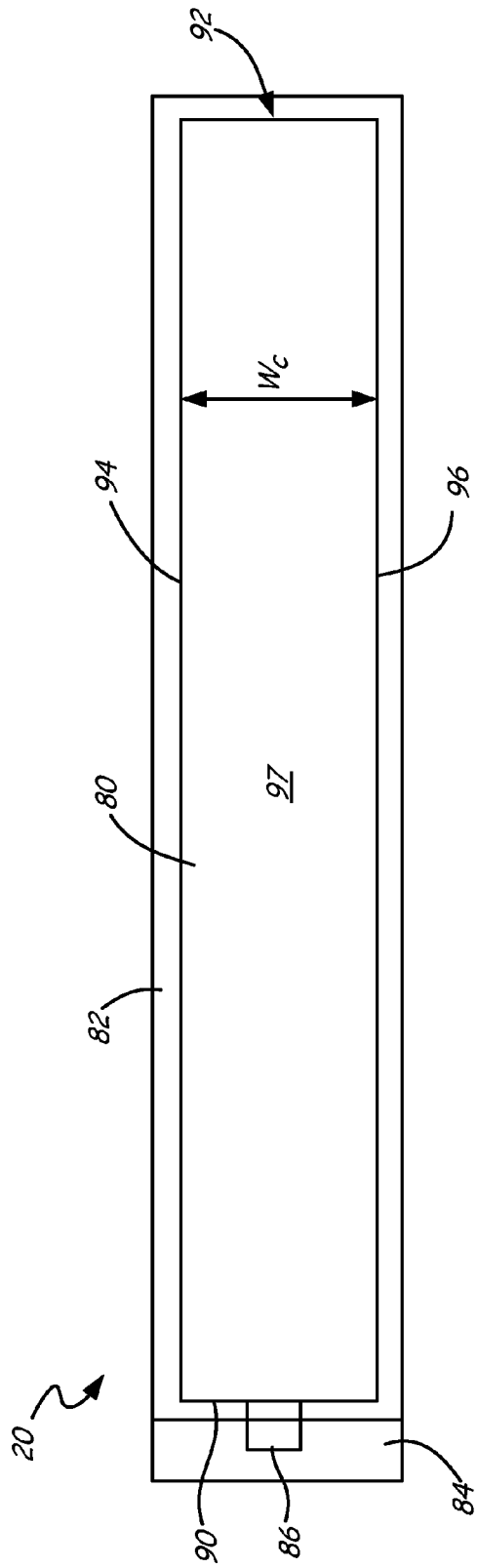
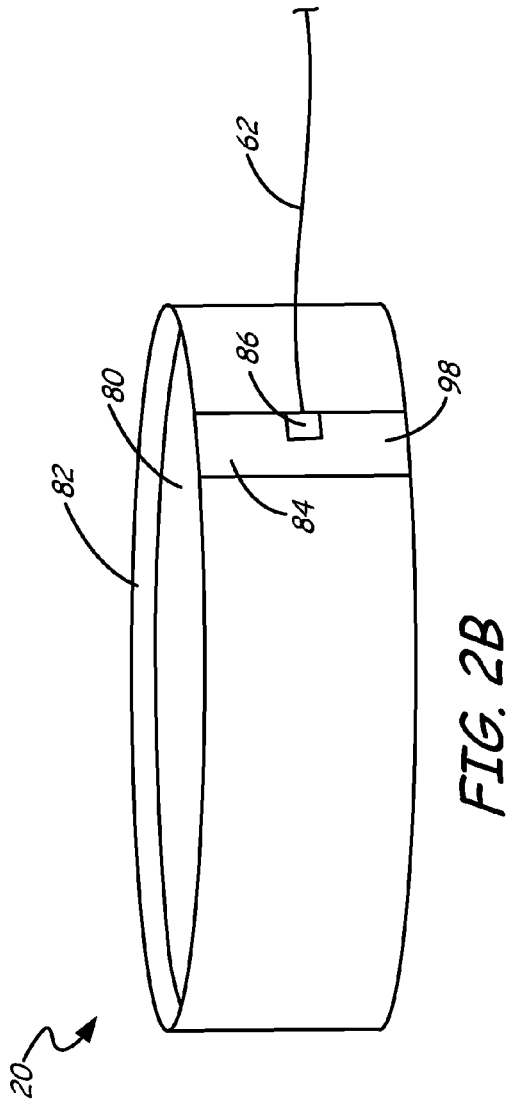

DISPERSIVE BELT FOR AN ABLATION SYSTEM

CROSS-REFERENCE TO RELATED APPLICATION

This application claims priority to Provisional Application No. 61/501,580, filed Jun. 27, 2011, which is herein incorporated by reference in its entirety.

TECHNICAL FIELD

The present invention relates to medical devices. More specifically, the invention relates to a dispersive belt in a system for ablating or otherwise treating tissue using electrical energy.

BACKGROUND

Thermal energy may be employed to ablate or otherwise treat tissue. The thermal energy may have a variety of forms, including radio frequency energy, microwave electromagnetic energy, laser energy, acoustic energy, or thermal conduction.

Radio frequency (RF) ablation may be used to treat patients with tissue anomalies. For example, cardiac ablation treatments involve the use of heat or freezing to create lesions in tissue to restore normal functioning of electrical activity near the tissue. Generally, cardiac ablation involves introducing a catheter into the heart where a therapeutic procedure can be carried out on abnormal heart tissue. RF ablation catheters employ electrodes at a distal end that can transfer RF or microwave electromagnetic energy to heart tissue. Catheter ablation may be used to treat atrial fibrillation and other types of heart rhythm disorders. RF ablation may also be used to treat other organs or tissue anomalies, such as cancer.

RF ablation devices generally direct electrical current from the active electrode on the catheter through the patient's body to a dispersive electrode that is externally attached to a location on the patient. The dispersive electrode, sometimes referred to as a neutral electrode, return electrode, or ground pad, provides a contact for RF signals to flow through the patient, where the current is dispersed to provide low current density through the dispersive electrode. The dispersive electrode may also provide a reference node for RF filters in the ablation system to reduce the effects of the RF energy on electrogram quality.

SUMMARY

Discussed herein is a dispersive electrode belt for use in a system for ablating or otherwise treating tissue using electrical energy, as well as electrosurgery systems including the dispersive electrode belt.

In Example 1, an electrosurgery system includes a catheter and a dispersive electrode assembly. The catheter includes one or more active electrodes adapted to be positioned adjacent biological tissue at an in vivo treatment site in a patient and to deliver electrical energy to the biological tissue. The dispersive electrode assembly includes a conductive element having a first end and a second end. The dispersive electrode assembly is configured to surround a waist of the patient such that a first surface of the conductive element is in contact with the waist and the first end of the conductive element is adjacent the second end of the conductive element.

In Example 2, the electrosurgery system according to Example 1, wherein the conductive element comprises first and second sides extending between the first end and second end, and wherein the first side is more proximate the one or more active electrodes than the second side.

In Example 3, the electrosurgery system according to either Example 1 or 2, wherein a distance between the one or more active electrodes and the first side of the dispersive electrode assembly is at least about 10 cm.

In Example 4, the electrosurgery system according to any of Examples 1-3, wherein a width of the conductive element between the first and second sides is between about 5 cm and about 50 cm.

In Example 5, the electrosurgery system according to any of Examples 1-4, wherein a length of the conductive element extends between the first and second sides, and wherein the length of the conductive element is at least about ten times greater than the width of the conductive element.

In Example 6, the electrosurgery system according to any of Examples 1-5, wherein the dispersive electrode assembly comprises a non-conductive structure coupled to a second surface of the conductive element to support the conductive element.

In Example 7, the electrosurgery system according to any of Examples 1-6, wherein the dispersive electrode assembly comprises a fastening mechanism to secure the dispersive electrode assembly around the waist.

In Example 8, the electrosurgery system according to any of Examples 1-7, wherein the fastening mechanism comprises a hook and loop fastener.

In Example 9, a dispersive electrode assembly for use in an electrosurgery system includes a conductive element having a first end and a second end. The conductive element is configured to surround a waist of a patient such that a first surface of the conductive element is in contact with the waist and the first end of the conductive element is adjacent the second end of the conductive element. The dispersive electrode assembly also includes a non-conductive structure coupled to a second surface of the conductive element to support the conductive element and secure the conductive element to the patient's waist.

In Example 10, the dispersive electrode assembly according to Example 9, wherein the conductive element comprises first and second sides extending between the first end and second end.

In Example 11, the dispersive electrode assembly according to either Example 9 or 10, wherein a width of the conductive element between the first and second sides is between about 5 cm and about 50 cm.

In Example 12, the dispersive electrode assembly according to any of Examples 9-11, wherein the dispersive electrode assembly comprises a fastening mechanism to secure the dispersive electrode assembly around the anatomical feature.

In Example 13, the dispersive electrode assembly according to any of Examples 9-12, wherein the fastening mechanism comprises a hook and loop fastener.

In Example 14, the dispersive electrode assembly according to any of Examples 9-13, wherein the conductive element comprises a malleable material selected from the group consisting of aluminum copper, silver, silver chloride, gold, and alloys thereof.

In Example 15, an electrosurgery system includes an energy source, a catheter, and a dispersive electrode assembly. The catheter is electrically connectable to the energy source and includes one or more active electrodes adapted to be positioned adjacent biological tissue at an in vivo treatment site in a patient and to deliver electrical energy from the energy source to the biological tissue. The dispersive electrode assembly includes a conductive element having a first end and a second end and is connectable to the energy source as a dispersive electrode. The dispersive electrode assembly is configured to surround a waist of the patient such that a first surface of the conductive element is in contact with the waist and the first end of the conductive element is adjacent the second end of the conductive element.

In Example 16, the electrosurgery system according to Example 15, wherein the conductive element comprises first and second sides extending between the first end and second end, and wherein the first side is more proximate the one or more active electrodes than the second side.

In Example 17, the electrosurgery system according to Example 15 or 16, wherein a width of the conductive element between the first and second sides is between about 5 cm and about 50 cm.

In Example 18, the electrosurgery system according to any of Examples 15-17, wherein a length of the conductive element extends between the first and second sides, and wherein the length of the conductive element is at least about ten times greater than the width of the conductive element.

In Example 19, the electrosurgery system according to any of Examples 15-18, wherein the dispersive electrode assembly comprises a non-conductive structure coupled to a second surface of the conductive element to support the conductive element.

In Example 20, the electrosurgery system according to any of Examples 15-19, wherein the dispersive electrode assembly comprises a fastening mechanism to secure the dispersive electrode assembly around the waist.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A is a plan view of an embodiment of a dispersive electrode for use in the electrosurgery system of FIG. 1 in a disengaged configuration.

FIG. 2B is a plan view of an embodiment of the dispersive electrode of FIG. 2A in an engaged configuration.

Figure 1:
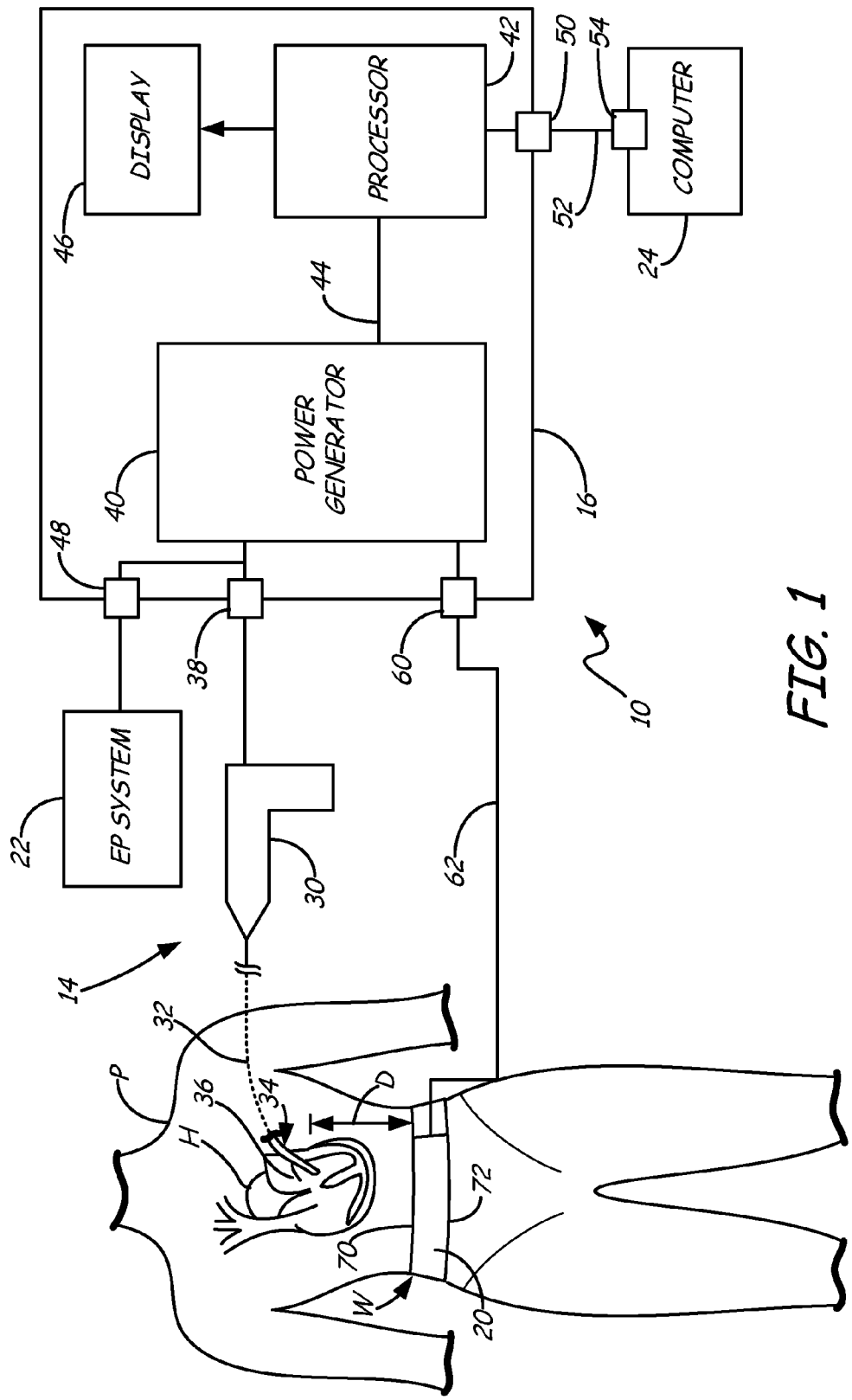
FIG. 1 shows an embodiment of an electrosurgery system including a dispersive electrode configured to surround a patient's waist.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows an embodiment of an electrosurgery system 10 for use in electrotherapy (e.g., ablation) of a biological site. In the embodiment shown, the biological site treated with the electrosurgery system 10 is a heart H of a patient P. While the following embodiments are described with reference to electrosurgical procedures of the heart H, the electrosurgery system 10 may alternatively be used to conduct electrosurgery on other biological sites or to treat diseases (e.g., cancer).

The electrosurgery system 10 includes a catheter system 14, a power control system 16, a dispersive electrode 20, an electrophysiological (EP) monitoring system 22, and a computer 24. The catheter system 14 provides current supplied by the power control system 16 to the heart H. In some embodiments, the power control system 16 supplies radio frequency (RF) current. The dispersive electrode 20, which will be described in more detail below, surrounds the waist W of the patient P and provides a path for RF current to flow between the active electrodes in the catheter system 14 and the power control system 16. The EP monitoring system 22 collects and displays electrograms (EGMs) from within the biological site, and the computer 24 displays, collects, and logs ablation data.

The catheter system 14 includes a handle 30 and a steerable catheter shaft 32 having a distal portion 34 that is configured to be introduced percutaneously into or adjacent to the heart H. The distal portion 34 of the catheter system 14 includes an electrode assembly 36 of one or more active electrodes. In some embodiments, the electrode assembly 36 includes a plurality of electrodes arranged in a substantially linear array along the distal portion of the catheter shaft 32. The electrodes may be arranged to include an electrically non-conductive space between adjacent electrodes. In some embodiments, the electrodes are band electrodes that wrap around the distal portion 34 of the catheter system 14. The catheter system 14 connects to the power control system 16 at a catheter interface 38.

The electrodes of the electrode assembly 36 may be formed of a material having a significantly higher thermal conductivity than that of the biological tissue to be ablated. Exemplary materials that may be suitable for the electrodes include, but are not limited to, silver, gold, chromium, aluminum, molybdenum, tungsten, nickel, platinum, platinum iridium, and alloys thereof. Because of the difference in thermal conductivity between the electrodes and the tissue, the electrodes cool off more rapidly in the flowing fluids at the biological site. In some embodiments, the electrodes are sized so that the surface area available for contact with fluid in the heart H (i.e., blood) is sufficient to allow for sufficient heat dissipation from the electrodes to the surrounding blood.

The electrode assembly 36 may also include one or more temperature sensors for monitoring the temperature of the electrode assembly 36. In some embodiments, each electrode in the electrode assembly 36 has a temperature sensor associated with it. Each temperature sensor provides a temperature signal to the processor 42 that is indicative of the temperature of the associated electrode. In other embodiments, some or all of the temperature sensors are associated with two or more electrodes.

It should be noted that the electrosurgery system 10 is not necessarily limited to the catheter system 14, and other devices that are capable of delivering RF energy may alternatively be employed in the electrosurgery system 10. In addition, other types of medical devices may also be used that are configured to deliver ultrasound energy, microwave energy, and/or other forms of energy for the purpose of electrosurgery.

The power control system 16 includes a power generator 40 that may include any number of output channels for providing power to the electrodes of the electrode assembly 36. The operation of the power generator 40 is controlled by a processor 42, which provides control signals to the power generator 40 via a communication conduit 44. The power control system 16 may also include a display 46 to display information relating to the operation of the power control system 16. For example, the display 46 may provide information relating to validation and troubleshooting set-up of the electrosurgery system 10, as described in U.S. Pat. No. 6,796,980, which is hereby incorporated by reference in its entirety for all purposes.

The processor 42 monitors the power provided by the power generator 40 through signals provided to the processor 42 via the communication conduit 44. In some embodiments, the processor 42 also monitors the temperatures of the electrodes within the electrode assembly 36 through signals provided by the power generator 40 via the communication conduit 44. Based on the monitored power and temperature, the processor 42 may adjust the power supplied by the power generator 36 to the electrodes. In some embodiments, power control methods that may be used in conjunction with the power control system 16 is described are disclosed in U.S. Pat. Nos. 6,050,994, 6,059,778, and 6,171,305, each of which is hereby incorporated by reference in its entirety for all purposes.

The EP monitoring system 22 connects to the power control system 16 via an EP monitoring system interface 48. The EP monitoring system interface 48 receives signals from the catheter system 14 via the catheter interface 38. The EP monitoring system 22 collects and displays EGMs from within the heart H through the electrode assembly 36 at the distal portion 34 of the catheter shaft 32. The EP monitoring system 22 breaks the signals received from the electrode assembly 36 into individual EGM signals for each electrode. The EGMs from the electrodes may be filtered and provided to a recorder in the EP monitoring system 22 where they are displayed for analysis (e.g., on the computer 24 or display 46). For a multi-electrode system, each electrode may be individually displayed. In an alternative embodiment, the electrode signals are filtered by the power control system 16 before being provided to the EP monitoring system 22.

The computer 24 connects to the computer interface 50 on the power control system 16 through a data connection 52. The data connection 52 may be connected to a data port 54, such as a RS232 port or other serial port, on the computer 24. The processor 42 outputs ablation data, including electrode temperature, power output voltage, and current measurements, to the computer 24 over the data connection 52. The computer 24 may then log the ablation data for subsequent review and analysis. The data may also be displayed by the computer 24.

Dispersive electrodes are used in electrosurgery, such as RF ablation, to complete the electrical circuit path from the electrode assembly 36 through the patient P. Many electrosurgery procedures employ high currents (e.g., greater than 1 A) constantly for an extended period of time (e.g., greater than ten minutes). The total energy that is thus dissipated by the dispersive electrode(s) is large, which can lead to heating of the dispersive electrode over the course of electrosurgery procedure. The dispersive electrode 20 in the electrosurgery system 10 is configured to prevent or reduce heating in the dispersive electrode 20 during electrosurgery procedures.

The dispersive electrode 20 is configured to surround the waist W of the patient P. That is, a first end of the dispersive electrode 20 couples to the patient P, and wraps around the patient's waist W such that a second end of the dispersive electrode 20 is adjacent to the first end. The end regions of the dispersive electrode 20 may overlap when the dispersive electrode 20 is secured to the patient. In some embodiments, the dispersive electrode 20 is configured as a belt for securing to the patient P. In alternative embodiments, the dispersive electrode 20 is configured to wrap around other anatomical features. When secured to the patient P, the dispersive electrode 20 allows fluoroscopy methods to be employed to facilitate positioning of the electrode assembly 36, since the dispersive electrode 20 does not interfere with imaging near the heart H.

The dispersive electrode 20 includes one or more conductors that couple to a dispersive electrode interface 60 on the power control system 16 via a conductor 62. The one or more conductors are secured against the patient, and a gel may be employed to improve conductive contact between the one or more conductors and the patient P. The dispersive electrode 20 provides a contact for the RF current from the electrode assembly 36 to flow through the patient P, where current is dispersed in the dispersive electrode 20. In addition, the dispersive electrode 20 provides a reference voltage for the electrosurgery system 10, including a reference voltage for filters associated with the EP monitoring system 22 to reduce the effects of the RF current on the quality of the EGM data.

To reduce the extent of heating in the dispersive electrode 20, the total surface area of the conductor in the dispersive electrode 20 in contact with the patient P is large. This allows the current in the dispersive electrode 20 to be dissipated over a larger region (i.e., around the entire waist of the patient P), thereby decreasing the maximum temperature of the dispersive electrode 20 during an electrosurgery procedure.

In addition, the current density in the dispersive electrodes is greatest at the edge of the dispersive electrodes closest to the electrode assembly 36 (i.e., the proximal edge 70), due to the edge effect. To reduce the magnitude of the current density at the proximal edge 70, the length of the proximal edge 70 of the dispersive electrode 20 extends around the patient P to provide a longer, electrically equivalent region over which to distribute energy and heat substantially evenly.

The distance D from the electrode assembly 36 to the proximal edge 70 of the dispersive electrode 20 also has an effect on the current density in the dispersive electrode 20. In some embodiments, the proximal edge 70 is at least about 10 cm from the electrode assembly 36. The edge effect may be enhanced when the distal edge 72 is significantly further from the proximal edge. The width should be chosen such that the maximum current density is barely dominated by the edge effect, where the current density is not significantly reduced via larger electrode width.

Another factor in the distribution of the current density in the dispersive electrode is the geometry of the electrode. For example, sharp angles and corners may result in an increase in current density in the area of the sharp angles or corners due to the fringe effect. This is most likely to occur when the sharp angles or corners are at the proximal edge of the dispersive electrode, since this provides for varying distances between the active electrodes and the side of the dispersive electrode closest to the active electrodes (due to a combination of the edge effect and fringe effect). This can result in concentrated heating in the area of the sharp angles or corners. To prevent this, the dispersive electrode 20 includes a continuous proximal edge with no sharp angles or corners to prevent high current densities in the dispersive electrode 20.

A further factor that may result in excessive heating in the dispersive electrode is improper or incomplete coupling of the dispersive electrode to the patient P. For example, if the dispersive electrode is not properly adhered to the patient, or physiological characteristics of the patient P (e.g., hair, skin oil, sweat) prevent the dispersive electrode from remaining properly adhered to the patient, excessive heating at the portions of the dispersive electrode coupled to the patient may occur. To assure consistent contact with the patient P through the electrosurgery procedure, in some embodiments, the dispersive electrode 20 is mechanically secured to the patient P. In other embodiments, the dispersive electrode 20 is chemically secured to itself when wrapped around the patient's waist W, but not chemically secured to the patient P.

FIG. 2A is a plan view of an embodiment of the dispersive electrode 20 in a disengaged configuration (i.e., prior to wrapping around the waist W of the patient P), and FIG. 2B is a plan view of the dispersive electrode 20 in an engaged configuration (i.e., after securing the dispersive electrode 20 around the patient's waist W). The dispersive electrode 20 includes a conductive element 80, a non-conductive support element 82, a securing mechanism 84, and a power control interface 86. The conductive element 80 is supported and carried by the support element 82. For example, the conductive element 80 may be chemically or mechanically secured to the support element 82. The power control interface 86 provides a conductive interface between the conductive element 80 and the conductor 62, which connects to the power control system 16.

In some embodiments, the conductive element 80 comprises a continuous sheet of conductive material. The conductive material is malleable to allow the dispersive electrode 20 to be wrapped around the patient P while maintaining the integrity and shape of the conductive element 80. In some embodiments, the conductive material comprises copper, silver, silver chloride, gold, aluminum, platinum, or any alloys thereof. In other embodiments, the conductive material comprises a conductive nanomaterial. While the dispersive electrode 20 is illustrated with a single conductive element 80, other embodiments of the dispersive electrode 20 may include two or more conductive elements.

The conductive element 90 includes a first end 90 and a second end 92. A proximal side or edge 94 and a distal side or edge 96 extend between the first end 90 and second end 92. The first and second ends 90, 92, and first and second sides 94, 96 define a first surface 97 and a second surface opposite the first surface 97 of the conductive element 80. To reduce current density variations along the proximal side 94 during an electrosurgery procedure, the proximal side 94 is substantially straight (i.e., does not include substantial contour variations, angles, or corners).

The conductive element 80 has a width $w_c$ that extends between the first and second sides 94, 96, and a length that extends between the first and second ends 90, 92. In some embodiments, the length of the conductive element is at least about ten times the width $w_c$. In other embodiments, the length of the conductive element is at least about 20 times the width $w_c$. In some embodiments, the width $w_c$ is between about 0.5 cm and 5.0 cm. While the conductive element 80 is shown having a rectangular shape in the disengaged configuration, other shapes and contours are also possible (e.g., oval).

The support element 82 is coupled to a second surface of the conductive element 80 opposite the first surface of the conductive element 80 shown in FIG. 2A. The support element 82 may completely or partially cover the second surface. In some embodiments, the support element 82 is comprised of a flexible material that can be easily decontaminated with the conductive element 80 and conductor 62, allowing for reuse of the dispersive electrode 20. In some embodiments, the support element 82 is comprised of a synthetic polymer. Alternatively, the support material 82 may be comprised of a disposable medical material in single-use embodiments of the dispersive electrode 20. The support material 82 may be configured to prevent inadvertent electrical contact to the outside of the belt, thereby preventing an alternate RF energy pathways.

The securing mechanism 84 is formed or provided on the support element 82 and facilitates securing of the dispersive electrode 20 to the patient P. Particularly, when the dispersive electrode 20 is wrapped around the patient, the securing mechanism 84 releasably couples the end regions (i.e., the regions proximate the ends 90 and 92) of the dispersive electrode 20 to each other. For example, in the embodiment shown in FIG. 2B, when the end regions of the support element 82 overlap, the securing mechanism 84 holds the overlapping portions 98 of the support element together, thereby securing the conductive element 80 against the patient P. In some embodiments, the securing mechanism 84 comprises a hook and loop assembly, which is configured to couple with a mating hook and loop assembly on the opposite side of the support element 82 when the dispersive electrode 20 is secured to the patient P. In other embodiments, the securing mechanism 84 comprises a buckle or other mechanical fastener. In further embodiments, particularly in single-use implementations, the securing mechanism 84 comprises an adhesive material that couples to the opposite side of the support element 82 when the dispersive electrode 20 is secured to the patient P.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrosurgery system comprising:
   a catheter including one or more active electrodes adapted to be positioned adjacent biological tissue at an in vivo treatment site in a patient and to deliver electrical energy to the biological tissue; and
   a dispersive electrode assembly including a conductive element having a first end and a second end, the conductive element comprising a single continuous sheet of conductive material, the dispersive electrode assembly configured to completely surround a waist of the patient such that, when the dispersive electrode assembly is completely surrounding the waist of the patient, a first surface of the conductive element wraps completely around, and is in contact with, the waist and the first end of the conductive element is adjacent the second end of the conductive element;
   wherein the dispersive electrode assembly comprises a non-conductive structure, having a first end region and a second end region, coupled to a second surface of the conductive element to support the conductive element; and
   wherein the dispersive electrode assembly further comprises a fastening mechanism, provided on the non-conductive structure, to secure the dispersive electrode assembly around the waist, wherein, when the dispersive electrode assembly is completely surrounding the waist of the patient, the end regions of the non-conductive structure overlap, and the fastening mechanism holds the overlapping end regions together.

2. The electrosurgery system of claim 1, wherein the conductive element comprises first and second sides extending between the first end and second end, and wherein the first side is more proximate the one or more active electrodes than the second side.

3. The electrosurgery system of claim 2, wherein a distance between the one or more active electrodes and the first side of the dispersive electrode assembly is at least 10 cm.

4. The electrosurgery system of claim 2, wherein a width of the conductive element between the first and second sides is between 0.5 cm and 5.0 cm.

5. The electrosurgery system of claim 4, wherein a length of the conductive element extends between the first and second sides, and wherein the length of the conductive element is at least ten times greater than the width of the conductive element.

6. The electrosurgery system of claim 1, wherein the fastening mechanism comprises a hook and loop fastener.

7. A dispersive electrode assembly for use in an electrosurgery system, the dispersive electrode comprising:
   a conductive element having a first end and a second end, wherein the conductive element comprises a single continuous sheet of conductive material and is configured to completely surround a waist of a patient such that, when the conductive element is completely surrounding the waist of the patient, a first surface of the conductive element is in contact with the waist and the first end of the conductive element is adjacent the second end of the conductive element;
   a non-conductive structure, having a first end region and a second end region, coupled to a second surface of the conductive element to support the conductive element and secure the conductive element to the waist; and
   a fastening mechanism, provided on the non-conductive structure, to secure the conductive element around the waist, wherein, when the conductive element is completely surrounding the waist of the patient, the end regions of the non-conductive structure overlap, and the fastening mechanism holds the overlapping end regions together.

8. The dispersive electrode assembly of claim 7, wherein the conductive element comprises first and second sides extending between the first end and second end.

9. The dispersive electrode assembly of claim 7, wherein a width of the conductive element between the first and second sides is between 0.5 cm and 5.0 cm.

10. The dispersive electrode assembly of claim 7, wherein the fastening mechanism comprises a hook and loop fastener.

11. The dispersive electrode assembly of claim 7, wherein the conductive element comprises a malleable material selected from the group consisting of aluminum copper, silver, silver chloride, gold, and alloys thereof.

12. An electrosurgery system comprising:
   an energy source;
   a catheter electrically connectable to the energy source, the catheter including one or more active electrodes adapted to be positioned adjacent biological tissue at an in vivo treatment site in a patient and to deliver electrical energy from the energy source to the biological tissue; and
   a dispersive electrode assembly including a conductive element having a first end and a second end, the conductive element comprising a single continuous sheet of conductive material and connectable to the energy source as a dispersive electrode, wherein the dispersive electrode assembly is configured to completely surround a waist of the patient such that, when the dispersive electrode assembly is completely surrounding the waist of the patient, a first surface of the conductive element wraps completely around, and is in contact with, the waist and the first end of the conductive element is adjacent the second end of the conductive element;
   wherein the dispersive electrode assembly comprises a non-conductive structure, having a first end region and a second end region, coupled to a second surface of the conductive element to support the conductive element; and
   wherein the dispersive electrode assembly further comprises a fastening mechanism, provided on the non-conductive structure, to secure the dispersive electrode assembly around the waist, wherein, when the dispersive electrode assembly is completely surrounding the waist of the patient, the end regions of the non-conductive structure overlap, and the fastening mechanism holds the overlapping end regions together.

13. The electrosurgery system of claim 12, wherein the conductive element comprises first and second sides extending between the first end and second end, and wherein the first side is more proximate the one or more active electrodes than the second side.

14. The electrosurgery system of claim 13, wherein a width of the conductive element between the first and second sides is between 0.5 cm and 5.0 cm.

15. The electrosurgery system of claim 14, wherein a length of the conductive element extends between the first and second sides, and wherein the length of the conductive element is at least ten times greater than the width of the conductive element.

* * * * *